(12) United States Patent
Huang et al.

(10) Patent No.: US 10,247,674 B2
(45) Date of Patent: Apr. 2, 2019

(54) INTEGRATED RAMAN SPECTRUM MEASUREMENT SYSTEM

(71) Applicant: PROTRUSTECH CO., LTD, Tainan (TW)

(72) Inventors: Chun-Ta Huang, Tainan (TW); Hsiu-Feng Tung, Tainan (TW); Wei-Hsin Wang, Tainan (TW)

(73) Assignee: PROTRUSTECH CO., LTD, Tainan (TW)

( * ) Notice: Subject to any disclaimer, the term of this patent is extended or adjusted under 35 U.S.C. 154(b) by 0 days.

(21) Appl. No.: 15/700,190

(22) Filed: Sep. 11, 2017

(65) Prior Publication Data

US 2017/0370850 A1    Dec. 28, 2017

Related U.S. Application Data

(63) Continuation of application No. 14/874,485, filed on Oct. 5, 2015, now abandoned.

(60) Provisional application No. 62/105,752, filed on Jan. 21, 2015.

(51) Int. Cl.
*G01N 21/65* (2006.01)
*G01J 3/02* (2006.01)
*G01J 3/44* (2006.01)

(52) U.S. Cl.
CPC .......... *G01N 21/65* (2013.01); *G01J 3/0235* (2013.01); *G01J 3/0256* (2013.01); *G01J 3/0291* (2013.01); *G01J 3/44* (2013.01); *G01N 21/658* (2013.01); *G01N 2201/0221* (2013.01)

(58) Field of Classification Search
CPC ............... G01N 21/65; G01N 21/658; G01N 2201/0221; G01J 3/44; G01J 3/0256; G01J 3/0235; G01J 3/0291; H01S 3/0405
See application file for complete search history.

(56) References Cited

U.S. PATENT DOCUMENTS

| 3,624,421 | A | * | 11/1971 | Pantell | ...................... | H01S 3/30 |
|---|---|---|---|---|---|---|
| | | | | | | 330/4.5 |
| 5,159,586 | A | * | 10/1992 | Yamashita | ........... | G11B 7/0925 |
| | | | | | | 250/201.1 |
| 5,570,697 | A | * | 11/1996 | Walker | ................. | A61B 5/0833 |
| | | | | | | 600/532 |
| 6,650,357 | B1 | * | 11/2003 | Richardson | ............... | G01J 3/10 |
| | | | | | | 348/80 |

(Continued)

FOREIGN PATENT DOCUMENTS

| CN | 102095718 | 6/2011 |
|---|---|---|
| CN | 102608098 | 7/2012 |

(Continued)

*Primary Examiner* — Mohamed K Amara
(74) *Attorney, Agent, or Firm* — JCIPRNET

(57) ABSTRACT

An integrated Raman spectrum measurement system and a modularized laser module are provided. The modularized laser module includes a laser emitter and an axis adjustment mechanism. The laser emitter is configured to emit a laser beam. The axis adjustment mechanism is connected to the laser emitter and configured to adjust at least two parameters of axis and orientation of the laser emitter. A beam splitter is disposed on the path of the laser beam. A signal collection unit is for collecting at least a part of a signal light from the beam splitter, wherein the signal light is converting by an object after receiving the part of the laser beam.

9 Claims, 6 Drawing Sheets

(56) References Cited

U.S. PATENT DOCUMENTS

| | | | | |
|---|---|---|---|---|
| 7,102,746 B2* | 9/2006 | Zhao | G01J 3/44 | 356/301 |
| 7,573,570 B2* | 8/2009 | Zhang | G01J 3/02 | 356/301 |
| 7,817,698 B2* | 10/2010 | Li | H01S 3/022 | 372/20 |
| 8,487,271 B2* | 7/2013 | Yokoi | G01N 21/6458 | 250/458.1 |
| 8,699,020 B1* | 4/2014 | Zhou | G01J 3/0264 | 356/301 |
| 9,285,575 B2* | 3/2016 | Xie | G01J 3/10 | |
| 9,341,515 B2* | 5/2016 | Schulte | G01J 3/0289 | |
| 10,067,058 B1* | 9/2018 | Brown | G01J 3/00 | |
| 2002/0025490 A1* | 2/2002 | Shchegolikhin | B41M 3/14 | 430/270.15 |
| 2005/0185178 A1* | 8/2005 | Gardner, Jr. | G01J 3/02 | 356/301 |
| 2005/0257912 A1* | 11/2005 | Monty | F28F 3/025 | 165/80.2 |
| 2006/0192969 A1* | 8/2006 | Marks | G01J 3/4412 | 356/451 |
| 2007/0002319 A1* | 1/2007 | Knopp | G01J 3/02 | 356/301 |
| 2007/0247620 A1* | 10/2007 | Koo | G01J 3/44 | 356/301 |
| 2008/0117421 A1* | 5/2008 | Yamaguchi | G01J 3/02 | 356/417 |
| 2008/0159351 A1* | 7/2008 | Li | H01S 3/022 | 372/53 |
| 2008/0228428 A1* | 9/2008 | Balss | G01N 21/65 | 702/137 |
| 2010/0020318 A1* | 1/2010 | Lee | G01J 3/02 | 356/301 |
| 2010/0085567 A1* | 4/2010 | Dottery | G01J 3/443 | 356/301 |
| 2011/0212512 A1* | 9/2011 | Wang | B82Y 20/00 | 435/288.7 |
| 2012/0290223 A1* | 11/2012 | Mertens | G01J 3/28 | 702/25 |
| 2013/0088709 A1* | 4/2013 | Koenig | G02B 21/0028 | 356/72 |
| 2015/0056645 A1* | 2/2015 | Vacca | G01N 15/1459 | 435/29 |
| 2015/0157286 A1* | 6/2015 | Wang | A61B 6/485 | 600/426 |
| 2015/0310969 A1* | 10/2015 | Chen | H01B 13/348 | 216/13 |
| 2016/0077008 A1* | 3/2016 | Takasu | A61B 5/0075 | 348/77 |
| 2016/0355869 A1* | 12/2016 | Blair | G01N 33/54373 | |
| 2017/0018415 A1* | 1/2017 | Zhao | G02B 21/0032 | |
| 2017/0328912 A1* | 11/2017 | Szlag | G01N 33/68 | |
| 2018/0000351 A1* | 1/2018 | Zharov | A61B 5/0095 | |
| 2018/0086002 A1* | 3/2018 | Sun | G02B 1/041 | |
| 2018/0243082 A1* | 8/2018 | Zheleznyak | A61F 9/00825 | |

FOREIGN PATENT DOCUMENTS

| | | |
|---|---|---|
| CN | 102636478 | 8/2012 |
| CN | 103743720 | 4/2014 |
| CN | 104040309 | 9/2014 |

* cited by examiner

INTEGRATED RAMAN SPECTRUM MEASUREMENT SYSTEM

CROSS REFERENCE TO RELATED APPLICATION

This application is a continuation application of and claims the priority benefit of U.S. application Ser. No. 14/874,485, filed on Oct. 5, 2015, which claims the priority benefit of U.S. provisional application Ser. No. 62/105,752, filed on Jan. 21, 2015. The entirety of each of the above-mentioned patent applications is hereby incorporated by reference herein and made a part of specification.

BACKGROUND OF THE INVENTION

1. Field of the Invention

The invention generally relates to an optical spectrometer and a light source module, in particular, to an integrated Raman spectrum measurement system and a modularized laser module.

2. Description of Related Art

A Raman spectrometer is a spectrometer used to observe vibrational, rotational, and other low-frequency modes in a system. Raman spectrometer is commonly used in chemistry to provide a fingerprint by which molecules can be identified.

It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system.

In the recent years, a micro Raman spectrometer is developed. However, the traditional micro Raman spectrometer is huge and has limited choice of laser wavelengths. Moreover, it is hard to adjust and set the positions of the lenses and mirrors in the micro Raman spectrometer.

SUMMARY OF THE INVENTION

Accordingly, the invention is directed to an integrated Raman spectrum measurement system, which is easy to set and operate.

The invention is directed to a modularized laser module, which is capable of adjust the position or orientation of a laser emitter in the light path.

An embodiment of the invention provides an integrated Raman spectrum measurement system configured to measure an object. The integrated Raman spectrum measurement system includes a modularized laser module, a beam splitter, and a signal collection unit. The modularized laser module includes a laser emitter and an axis adjustment mechanism. The laser emitter is configured to emit a laser beam. The axis adjustment mechanism is connected to the laser emitter and configured to adjust at least two parameters of axis and orientation of the laser emitter. The beam splitter is disposed on the path of the laser beam. The signal collection unit is for collecting at least a part of a signal light from the beam splitter, wherein the signal light is converting by the object after receiving the part of the laser beam.

An embodiment of the invention provides a modularized laser module including a laser emitter, an axis adjustment mechanism, and cooling fins. The laser emitter is configured to emit a laser beam. The axis adjustment mechanism is connected to the laser emitter and configured to adjust at least two parameters of axis and orientation of the laser emitter. The cooling fins are connected to the laser emitter.

An embodiment of the invention provides a portable integrated Raman spectrum measurement system. The portable integrated Raman spectrum measurement system includes a laser emitter, an axis adjustment mechanism, a beam splitter, a signal collection unit, an illumination device, an image switch module, and an image pickup device. The laser emitter is configured to emit a laser beam. The axis adjustment mechanism is connected to the laser emitter and configured to adjust at least two parameters of axis and orientation of the laser emitter. The beam splitter is disposed on the path of the laser beam. The signal collection unit is for collecting at least a part of a signal light from the beam splitter, wherein the signal light is converted by the object after receiving the part of the laser beam. The illumination device is configured to emit an illumination beam. The image switch module is adapted to be switched into the path of the laser beam or be switched out of the path of the laser beam. The image pickup device is for receiving an image beam from the object when the image switch module is switched into the path of the laser beam.

In the integrated Raman spectrum measurement system according to the embodiment of the invention, since the axis adjustment mechanism can adjust at least two parameters of axis and orientation of the laser emitter, and the modularized laser module is used, the setting and adjustment of the light path in the integrated Raman spectrum measurement system may be easily achieved by the modularized. As a result, the integrated Raman spectrum measurement system is easy to set and operate. In the modularized laser module, since the axis adjustment mechanism is used, the axes or orientations of the laser emitter in modularized laser module can be adjusted, which improves the applicability of the modularized laser module. In the integrated Raman spectrum measurement system according to the embodiment of the invention, since the image switch module is adapted to be switched into the path of the laser beam or be switched out of the path of the laser beam, a user can easily switch the integrated Raman spectrum measurement system to a measurement mode or an observation mode. As a result, the integrated Raman spectrum measurement system is easy to operate.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
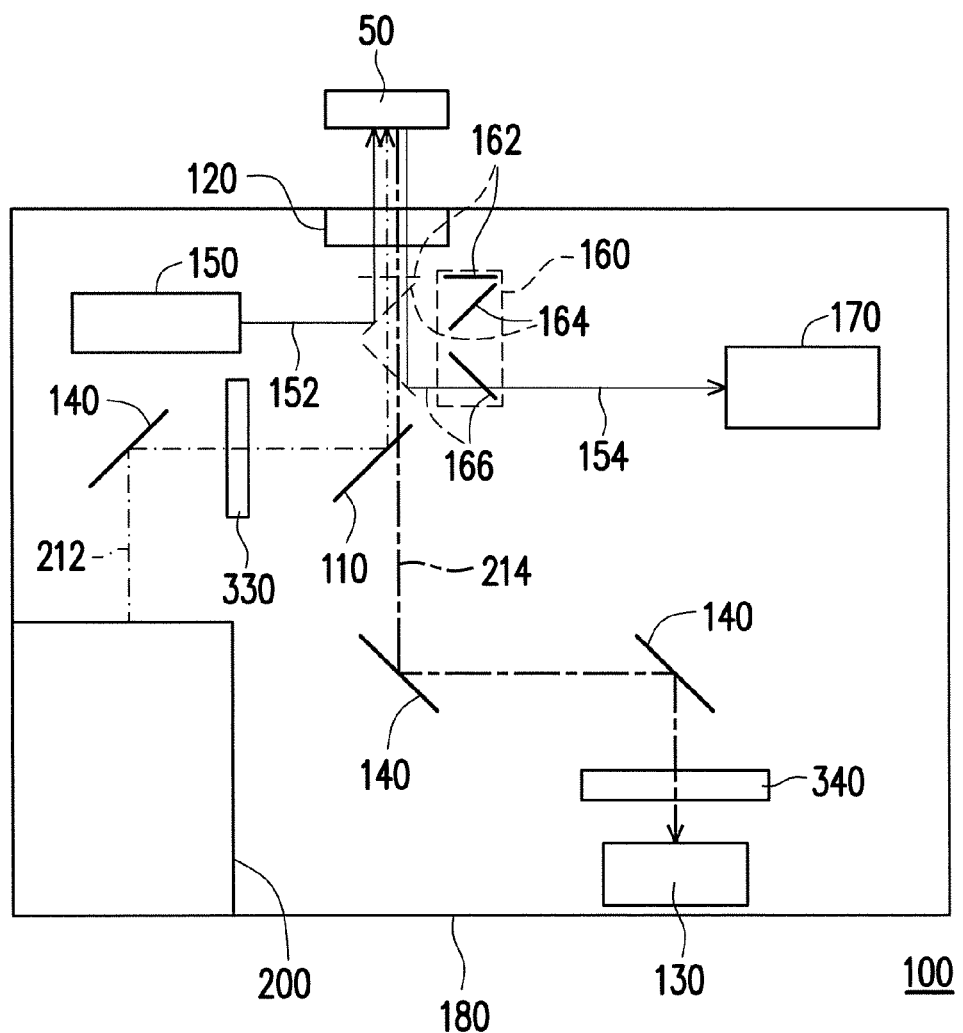
FIG. 1A is a schematic light path diagram of a Raman spectrometer according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

Figure 1B:
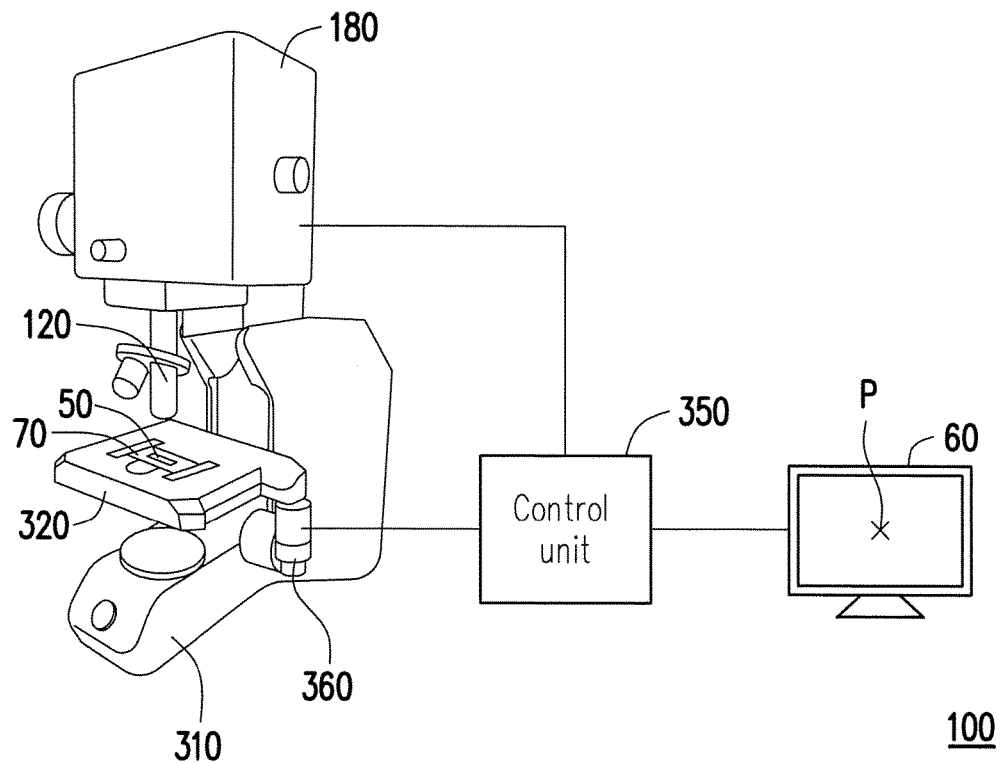
FIG. 1B is a schematic perspective view of the integrated Raman spectrum measurement system in FIG. 1A used in vertical mode.
Figure 1C:
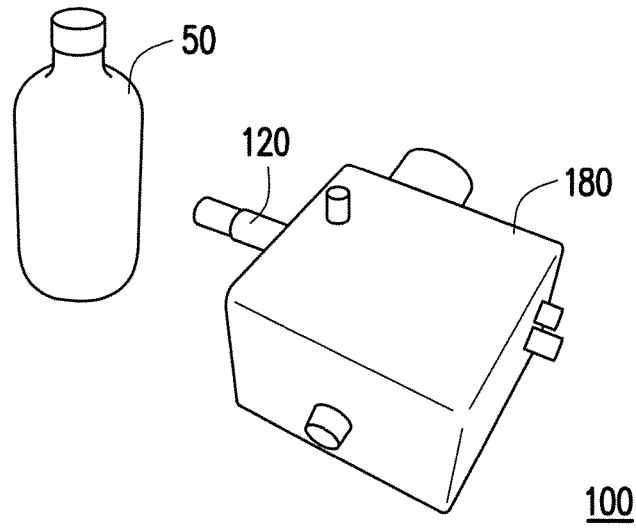
FIG. 1C is a schematic perspective view of the integrated Raman spectrum measurement system in FIG. 1A used in horizontal mode.
Figure 2:
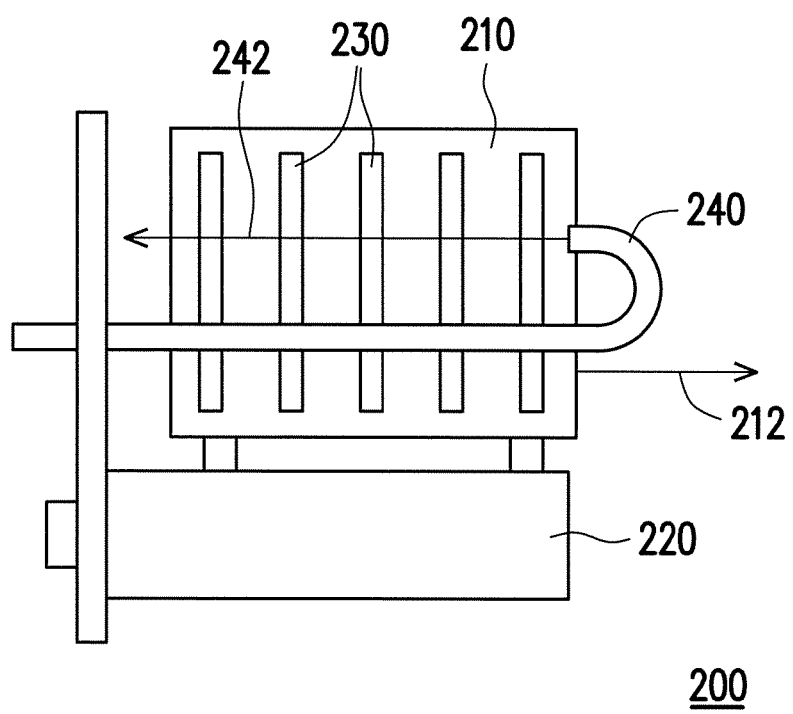
FIG. 2 is a schematic view of the modularized laser module in FIG. 1A.

FIG. 1A is a schematic light path diagram of an integrated Raman spectrum measurement system according to an embodiment of the invention, FIG. 1B is a schematic perspective view of the integrated Raman spectrum measurement system in FIG. 1A used in vertical mode, and FIG. 1C is a schematic perspective view of the integrated Raman spectrum measurement system in FIG. 1A used in horizontal mode. FIG. 2 is a schematic view of the modularized laser module in FIG. 1A. Referring to FIGS. 1A-1C and 2, an integrated Raman spectrum measurement system 100 in this embodiment is configured to measure an object 50. The integrated Raman spectrum measurement system 100 includes a modularized laser module 200, a beam splitter 110, an objective lens 120, and a signal collection unit 130. The modularized laser module 200 includes a laser emitter 210 and an axis adjustment mechanism 220. The laser emitter 210 is configured to emit a laser beam 212. In this embodiment, the laser emitter 210 is a laser diode or a diode-pumped solid-state (DPSS) laser. However, in other embodiment, the laser emitter 210 may be any other appropriate type of laser. The axis adjustment mechanism 220 is connected to the laser emitter 210 and configured to adjust at least two parameters of axis and orientation of the laser emitter 210. In this embodiment, the axis adjustment mechanism 220 is configured to move the laser emitter 210 along three axes which are perpendicular to each other. However, in other embodiments, the axis adjustment mechanism 220 may also rotate the laser emitter 210 around three axes which are perpendicular to each other. The aforementioned parameters of axis and orientation means the position parameters include, for example, the three axes of XYZ, and the rotation orientations around any axes. The adjusting at least two parameters of axis and orientation means that the laser emitter 210 may be adjusted at least in the two axes, in one axis and one orientation, or in two orientations, or any combinations thereof.

The laser beam 212 is transmitted from the laser emitter 210, and then transmitted into the object 50, a sample to be measured, through the bean splitter 110 and the objective lens 120. In one embodiment according to the present invention, the objective lens 120 is a device detachably mounted on the integrated Raman spectrum measurement system 100 on the optical path of the laser beam 212. The beam splitter 110 is also disposed on the path of the laser beam 212, transmitting at least part of the laser beam 212 to the object 50. In one embodiment, the beam splitter 110 may be a partially transmissive and partially reflective mirror, and in another embodiment, the beam splitter 110 may be a polarizing beam splitter.

The object 50 then converts at least part of laser beam 212 into a signal light 214. The objective lens 120 also transmits the signal light 214 to the beam splitter 110 which transmits at least part of the signal light 214 to the signal collection unit 130. In one embodiment, the beam splitter 110 may be the partially transmissive and partially reflective mirror, allowing a part of the signal light 214 to pass through and to be transmitted to the signal collection unit 130.

In one embodiment, the signal collection unit 130 may be a collimator which collimates the signal light 214 and transmits the signal light 214 to a spectroscope. However, in another embodiment, the signal collection unit 130 may be a spectroscope.

In one embodiment, a plurality of mirrors 140 disposed on the paths of the laser beam 212 and the signal light 214 turn the paths of the laser beam 212 and the signal light 214.

Since the axis adjustment mechanism 220 can adjust at least two parameters of axis and orientation of the laser emitter 210, which can significantly reduce to adjust of the beam splitter 110, the objective lens 120, and other optical components, e.g. the mirrors 140, in the integrated Raman spectrum measurement system 100 As a result, the integrated Raman spectrum measurement system 100 is easy to set and operate.

In addition, the modularized laser module 200 may be easy to be replaced by another modularized laser module 200 with a laser emitter 210 emitting different wavelength. As a result, the integrated Raman spectrum measurement system 100 is easily to be applied in the different measurement with various wavelengths. In one embodiment, the modularized laser module 200 can integrated with different laser emitter 210 emitting the different wavelength in 405, 473, 488, 532, 633, 785, 808 or 1064 nanometer (nm).

In one embodiment, the modularized laser module 200 further includes cooling fins 230 and a cooling gas tube 240 to improve the stability and reliability. The cooling fins 230 are connected to the laser emitter 210, and the cooling gas tube 240 is configured to supply cooling gas 242 flowing through the cooling fins 230. In an embodiment, a gas pump may be connected to one end of the cooling gas tube 240 to supply cooling gas into the cooling gas tube 240, and the cooling gas then exits from the other end of the cooling gas tube 240 and flows through the cooling fins 230.

In one embodiment, the integrated Raman spectrum measurement system 100 further includes an illumination device 150 for providing the illumination beam 152, an image switch 160 comprising a first beam splitter 164 and a second beam splitter 166, and an image pickup device 170. In one embodiment, the illumination device 150 may include at least one light-emitting diode (LED). The image switch module 160 can be switched into or out of the path of the laser beam 212. When the image switch module 160 is switched into the path of the laser beam 212, first beam splitter 164 (shown by dotted line in FIG. 1A) reflects at least part of the illumination beam 152 to the object 50 through the objective lens 120, then object 50 converts the at least part of the illumination beam 152 into an image beam 154 transmitted to the image switch module 160 through also the objective lens 120, and the second beam splitter 166 (shown by dotted line in FIG. 1A) reflects at least part of the image beam 154 to the image pickup device 170. In one embodiment, the first beam splitter 164 or second beam splitter 166 is a partially transmissive partially reflective mirror or a polarizing beam splitter.

In one embodiment, the image switch module 160 further includes a neutral density filter 162. When the image switch module 160 is switched into the path of the laser beam 212, the neutral density filter 162 (shown by dotted line in FIG. 1A) is also shifted to the path of the laser beam 212 to reduce intensity of the laser beam 212.

The image switch module 160 is easy to be switched into or out of the path of the laser beam 212, making users easily switch the integrated Raman spectrum measurement system to a measurement mode or an observation mode. Specifically, in the measurement mode, the neutral density filter 162, the first beam splitter 164 and the second beam splitter 166 are located at the positions of the solid lines in FIG. 1A, so that the signal light 214 may be transmitted to the signal collection unit 130, and the Raman signal of the object 50 may be measured. In the observation mode, the neutral density filter 162, the first beam splitter 164 and the second beam splitter 166 are located at the positions of the dotted lines in FIG. 1A, so that the image beam 154 may be transmitted to the image pickup device 170, and the image of the object 50 may be observed by the user through the image pickup device 170. In one embodiment, the image pickup device 170 is, for example, a camera. In another embodiment, the image pickup device 170 may be replaced by an eyepiece, so that the user may observe the image of the object 50 through the eyepiece.

Figure 3A:
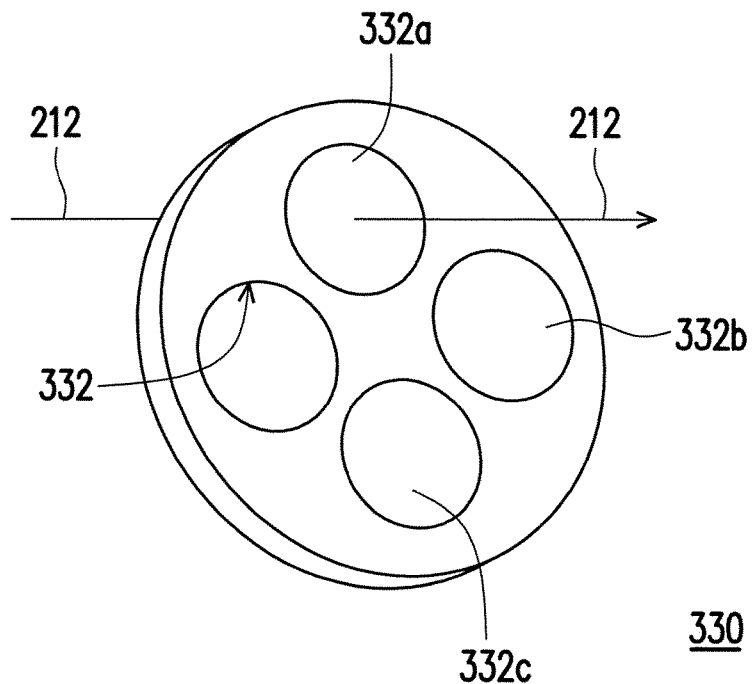
FIG. 3A is a schematic view of the neutral density filter module in FIG. 1A.

In one embodiment, the integrated Raman spectrum measurement system 100 further includes a neutral density filter module 330 disposed on the path of the laser beam 212 between the laser emitter 210 and the beam splitter 110, as shown in FIGS. 1A and 3A. The neutral density filter module 330 includes a plurality of neutral density filters 332a, 332b, 332c having different transmittance and configured to be selectively switched into the path of the laser beam 212. For example, the neutral density filter 332a may have the transmittance of ½, the neutral density filter 332b may have the transmittance of 1/10, and the neutral density filter 332c may have the transmittance of 1/100. Moreover, the neutral density filter module 330 may also have a hole 332 having the transmittance of 100%. The neutral density filters 332a, 332b, and 332c and the hole 332 may be switched into the path of the laser beam 212, so as to adjust the intensity of the laser beam 212. The number of the neutral density filters 332a, 332b, and 332c in the neutral density filter module 330 is not limited to 3. In other embodiment, the number of the neutral density filter(s) may be any natural number other than 3.

Figure 3B:
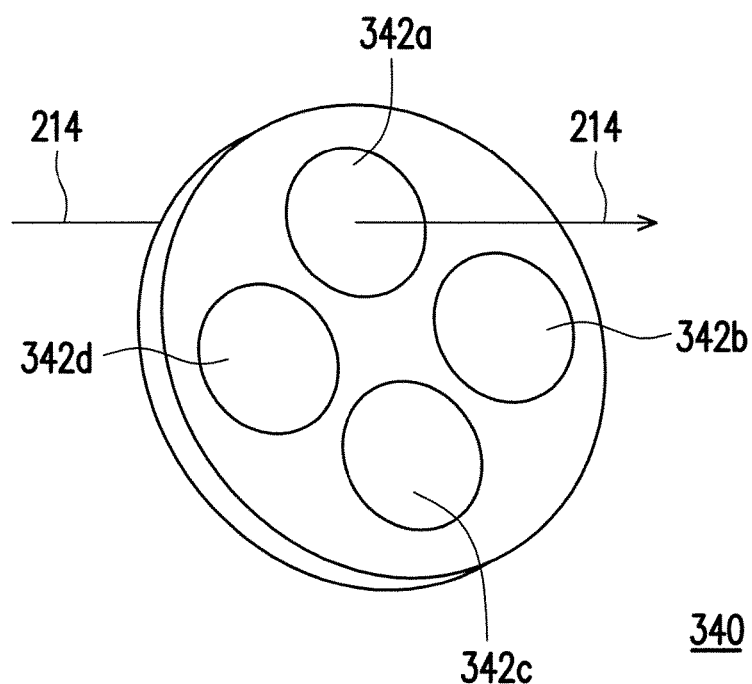
FIG. 3B is a schematic view of the Raman filter module in FIG. 1A.

In one embodiment, the integrated Raman spectrum measurement system 100 further includes a Raman filter module 340 disposed on a path of the signal light 214 between the beam splitter 110 and the signal collection unit 130, as shown in FIGS. 1A and 3B. The Raman filter module 340 includes a plurality of filters 342a, 342b, 342c, and 342d with different transmittance spectra, each of the filters 342a, 342b, 342c, and 342d is configured to filter out light having a wavelength range corresponding to the peak wavelength of the laser beam 212 of different laser emitter 210, and the filters 342a, 342b, 342c, and 342d are configured to be selectively switched into the path of the signal light 214. For example, when the peak wavelength of the laser beam 212 is 473 nm, the filter 342a capable of filtering out the light having the wavelength of 473 nm may be selected to switch into the path of the signal light 214 so as to filter out the portion having the wavelength of 473 nm in the signal light 214. The number of the filters in the Raman filter module 340 is not limited to 4. In other embodiments, the number of the filter(s) may be any natural number other than 4.

In one embodiment, the integrated Raman spectrum measurement system 100 further includes a housing 180, a pedestal 310 (see FIG. 1B), and a stage 320 (see FIG. 1B). The housing 180 contains the modularized laser module 200, the beam splitter 110, and the signal collection unit 130. In one embodiment, the housing 180 may further contains the image switch module 160, the illumination device 150, the image pickup device 170, and the mirrors 140. The pedestal 310 is detachably connected to the housing 180, and the stage 320 is movably connected to the pedestal 310 and configured to carry the object 50. When the pedestal 310 is attached to the housing 180 as shown in FIG. 1B, the integrated Raman spectrum measurement system 100 is used to measure the object 50 in a vertical mode. When the pedestal 310 is detached from the housing 180 as shown in FIG. 1C, the integrated Raman spectrum measurement system 100 is used to measure the object 50 in a horizontal mode.

In one embodiment, the integrated Raman spectrum measurement system 100 further includes a control unit 350 and a locating mechanism 360. The control unit 350 is electrically connected to the image pickup device 170, and the locating mechanism 360 is electrically connected to the control unit 350. The stage 320 connected to the locating mechanism 360. When a user selects a measuring point P on a screen 60 electrically connected to the control unit 350, the control unit 350 commands the locating mechanism 360 to move the stage 320 so that the measuring point P is shown in a central portion or a setting portion on the screen 60. In this embodiment, the user can select the measuring point P by using a mouse, a touch pen, finger touching, etc. Moreover the image shown on the screen 60 is the image detected by the image pickup device 170.

In one embodiment, a calibration plate having, for example, a smooth surface may be disposed on the stage 320 first. The calibration plate may reflects the laser beam 212, so that there is a clear light spot on the screen 60. Then, the user may selects the clear light spot as the measuring point P and mark the measuring point P. After that, the calibration plate is replaced by the object 50, and the position of the mark on the image of the object 50 is the measuring point P of the object 50. That is, the measured Raman signal is from the measuring point P of the object 50. The user may manually or automatically move the stage 320, so that the position on the object 50 which is regarded as the measuring point P is changed.

The integrated Raman spectrum measurement system 100 in this embodiment has the characteristic of small size, flexible wavelength switching, and in-situ analysis. The integrated Raman spectrum measurement system 100 can be applied to very small samples, built in surface enhanced Raman scattering technique, and the Raman spectra can be measured through quartz, glass, plastic.

Figure 4:
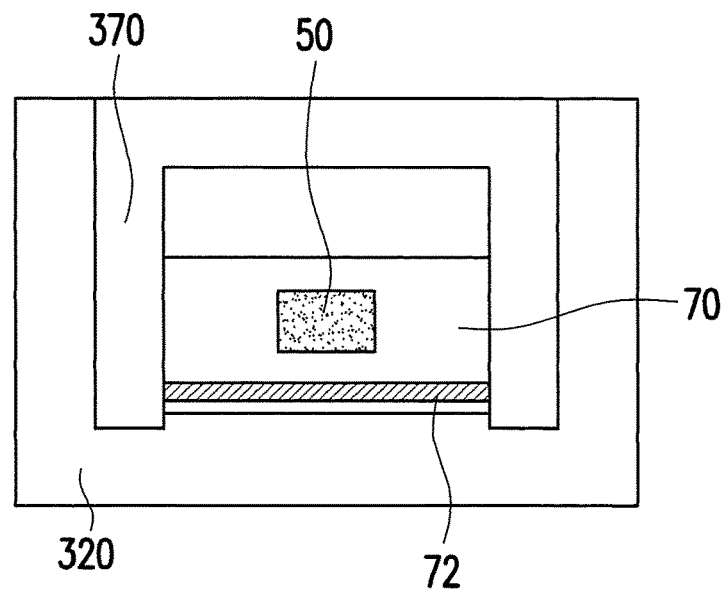
FIG. 4 is a schematic top view of a stage in another embodiment.

FIG. 4 is a schematic top view of a stage in another embodiment. Referring to FIGS. 1A, 1B, 2, and 4, in this embodiment, the integrated Raman spectrum measurement system 100 further includes a trigger 370 disposed on the stage 320. When the object 50 is disposed on the stage 320, the trigger 370 turns on the laser emitter 210 to emit the laser beam 212. In this embodiment, the object 50 is disposed on a microslide 70, and a conductive line 72 is formed on the microslide 70. When the microslide 70 is disposed on the stage 320 and the conductive line 72 touches the trigger 370, a closed circuit is formed so as to turns on the laser emitter 310 and the spectroscope connected to or located on the signal collection unit 130. That is, when the object 50 is disposed on the stage 320, the measurement is automatically started. In another embodiment, the trigger 370 may be a button, and when the microslide 70 is disposed on the stage 320, the microslide 70 presses the button, so as to turn on the laser emitter 310 and the spectroscope.

Figure 5:
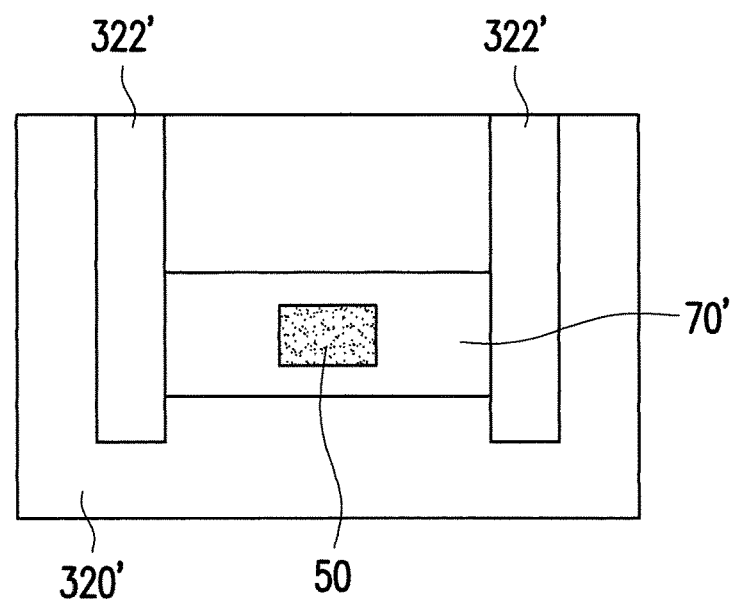
FIG. 5 is a schematic top view of a stage in another embodiment.

FIG. 5 is a schematic top view of a stage in another embodiment. Referring to FIG. 5, in this embodiment, the stage 320' is configured to supply an electric voltage or current to the object 50. Specifically, in this embodiment, the microslide 70' may be a conductive microslide or have a conductive patterns, and the electrodes 322' of the stage 320' supply the electric voltage or current to the microslide 70' so as to supply the electric voltage or current to the object 50. The electric voltage or current may activate the object 50, such as a bio-sample, so as to enhance the spectral signal of the bio-sample. Moreover, through the electrodes 322', the integrated Raman spectrum measurement system 100 may read the information of the bio-sample.

Figure 6:
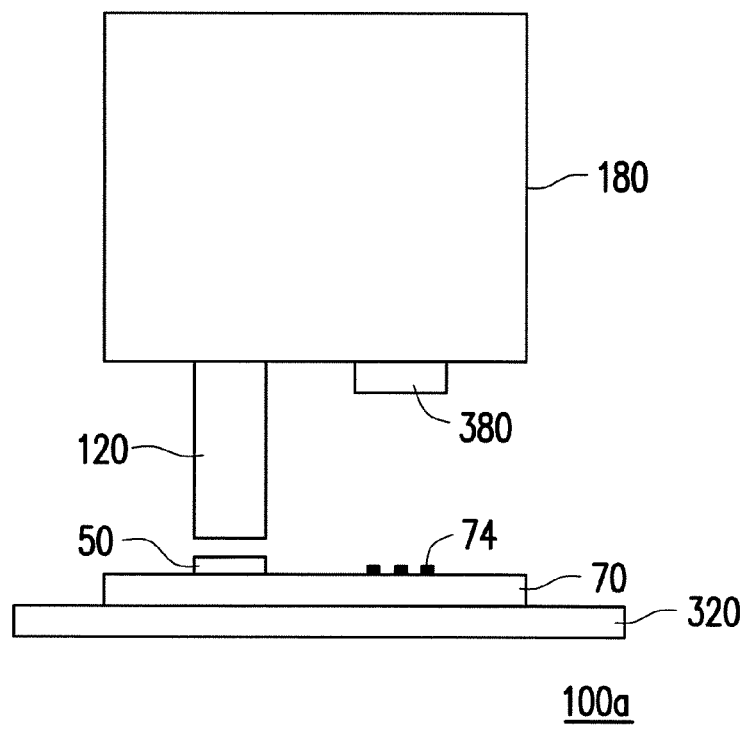
FIG. 6 is a schematic view of an integrated Raman spectrum measurement system according to another embodiment of the invention.

FIG. 6 is a schematic view of an integrated Raman spectrum measurement system according to another embodiment of the invention. Referring to FIG. 6, the integrated Raman spectrum measurement system 100a in this embodiment is similar to the integrated Raman spectrum measurement system 100 shown in FIG. 1B, and the main difference therebetween is as follows. In this embodiment, the integrated Raman spectrum measurement system 100a further includes a barcode scanner 380 configured to detect a barcode 74 of the object 50. The barcode scanner 380 may be electrically connected to the control unit 350, and the control unit 350 may identify the object 50 through the barcode 74. The measuring result can be integrated with the sample information in the barcode, and is then sent to a database. The barcode 74 may be a one-dimensional barcode or a two dimensional barcode, e.g. a quick response code (QR code). In another embodiment, the barcode 74 may be detected by the objective lens 120 and the image pickup device 170, and the integrated Raman spectrum measurement system 100 does not have the barcode scanner 380.

Figure 7:
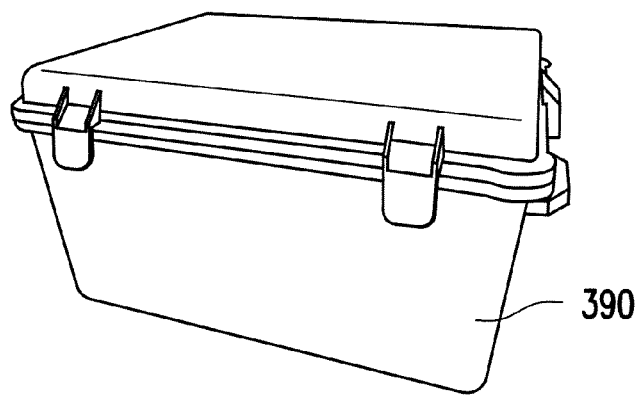
FIG. 7 is a schematic perspective view of an integrated Raman spectrum measurement system according to another embodiment of the invention.

FIG. 7 is a schematic perspective view of an integrated Raman spectrum measurement system according to another embodiment of the invention. Referring to FIGS. 1A, 1B, and 7, in this embodiment, the pedestal 310 is configured to serve as a case 390 of the integrated Raman spectrum measurement system 100 to contain the stage 320 and the housing 180. For example, the pedestal 310 may be transformed into the case 390, and the case 390 may serve as a corrosion prevention box. In another embodiment, the pedestal 310, the stage 320, and the housing 180 may be put into the case 390 serving as a corrosion prevention box. As a result, the integrated Raman spectrum measurement system 100 may be portable.

In conclusion, in the integrated Raman spectrum measurement system according to the embodiment of the invention, the modularized laser module is used and integrated with the axis adjustment mechanism to only adjust few parameters of axis and orientation of the laser emitter to easily achieve the setting and adjustment of the light path in the integrated Raman spectrum measurement system. In the integrated Raman spectrum measurement system according to the embodiment of the invention, since the image switch module is adapted to be switched into the path of the laser beam or be switched out of the path of the laser beam, a user can easily switch the integrated Raman spectrum measurement system to a measurement mode or an observation mode. As a result, the integrated Raman spectrum measurement system is easy to operate.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. An integrated Raman spectrum measurement system, comprising:
    a plurality of mirrors disposed on a beam path;
    a beam splitter disposed on the beam path, used to transmit at least a part of a laser beam on the beam path to an object and transmit a light signal from the object to a signal collection unit;
    a modularized laser module comprising:
        a laser emitter for emitting the laser beam; and
        an axis adjustment unit connected to the laser emitter and used to operably move the laser emitter along three axes of XYZ or operably rotate the laser emitter around the three axes of XYZ, so as to adjust the laser beam transmitted into the beam path; and
    a housing used to contain the plurality of mirrors, the modularized laser module, and the beam splitter, wherein the housing is detachably connected to a pedestal, and the modularized laser module is independently replaceable into the housing without replacing the beam splitter or the signal collection unit, and the laser emitter is moved or rotated within the housing.

2. The integrated Raman spectrum measurement system according to claim 1, further comprising:
    an objective lens mounted on the housing, used to transmit at least a part of the laser beam to the object and transmit the light signal to the beam splitter.

3. The integrated Raman spectrum measurement system according to claim 1, further comprising:
    an illumination device used to emit an illumination beam to the object;
    an image switch module being controlled to switch into or out of the beam path; and
    an image pickup device used to receive an image signal from the object as the image switch module is switched into the beam path.

4. The integrated Raman spectrum measurement system according to claim 3, wherein the image switch module comprises a neutral density filter, and as the image switch module is switched into the beam path, the neutral density filter is also switched into the beam path to reduce intensity of the laser beam transmitted into the image pickup device.

5. The integrated Raman spectrum measurement system according to claim 1, further comprising:
    a control unit electrically connected to an image pickup device;
    a locating mechanism electrically connected to the control unit; and
    a stage used to carry the object and connected to the locating mechanism;
    wherein the control unit commands the locating mechanism to move the stage as a user selects a measuring point on a screen electrically connected to the control unit, so that the measuring point is shown in a central portion or a setting portion on the screen.

6. The integrated Raman spectrum measurement system according to claim 1, further comprising a neutral density filter module disposed on the beam path, wherein the neutral density filter module comprises a plurality of neutral density filters having different transmittance and configured to be selectively switched into the beam path.

7. The integrated Raman spectrum measurement system according to claim 1, further comprising a stage used to carry the object and provide an electric voltage or current to the object.

8. The integrated Raman spectrum measurement system according to claim 1, wherein the pedestal is a portable case, and the housing can be detached from the pedestal and placed into the pedestal.

9. The integrated Raman spectrum measurement system according to claim 1, further comprising a trigger disposed on a stage, used to turn on the integrated Raman spectrum measurement system as the object is disposed on the stage.

\* \* \* \* \*